US005518730A

United States Patent [19]
Fuisz

[11] Patent Number: 5,518,730
[45] Date of Patent: May 21, 1996

[54] BIODEGRADABLE CONTROLLED RELEASE FLASH FLOW MELT-SPUN DELIVERY SYSTEM

[75] Inventor: Richard C. Fuisz, Great Falls, Va.

[73] Assignee: Fuisz Technologies Ltd., Chantilly, Va.

[21] Appl. No.: 893,238

[22] Filed: Jun. 3, 1992

[51] Int. Cl.$^6$ .......................... A61K 9/70; A61K 47/30; A61L 15/62

[52] U.S. Cl. .................. 424/426; 424/444; 424/451; 424/489; 424/449; 424/435; 424/436; 424/434; 424/45; 424/423; 424/438; 424/465; 424/439; 424/484; 424/9.4; 424/DIG. 13; 424/DIG. 15; 602/48

[58] Field of Search .............................. 424/426, 444, 424/452, 468; 425/9

[56] References Cited

U.S. PATENT DOCUMENTS

| | | | |
|---|---|---|---|
| 2,918,404 | 12/1969 | Mende et al. | 167/58 |
| 3,131,428 | 5/1964 | Mika | 18/8 |
| 3,299,568 | 1/1967 | Tobolsky | 47/9 |
| 3,308,221 | 3/1967 | Opfell | 264/174 |
| 3,324,061 | 6/1967 | Tanquary et al. | 260/29.2 |
| 3,332,926 | 7/1967 | Baron | 260/93.7 |
| 3,454,510 | 7/1969 | Newland | 260/23 |
| 3,590,528 | 7/1971 | Shepherd | 47/9 |
| 3,592,792 | 7/1971 | Newland | 260/41 |
| 3,625,214 | 12/1971 | Higuchi | 128/260 |

(List continued on next page.)

FOREIGN PATENT DOCUMENTS

| | | |
|---|---|---|
| PCT/WO91/ 18613 | 12/1991 | European Pat. Off. . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |

OTHER PUBLICATIONS

Schacht, E., "Using Biodegradable Polymers in Advanced Drug Delivery Systems", *Medical Device Technology* (Jan./Feb. 1990).

Kulkarni, et al., "Polyactic Acid SurgicalImplants" *Arch. Surg.*, vol.93 (Nov., 1966).

Vert, M., "Bioresorbable Polymers For Temporary Therapeutic Applications" *Angew MaKromol Chem.*, pp. 166–167 (1989).

Dimitriu et al., "Polymeric Biomaterials As Enzyme and Drug Carriers Part V: Polymeric Matrices as Drug Delivery Systems", *Bioactive and Compatible Polymers*, (Jan., 1990).

Kohn, et al., "The Ring–Opening Polymerization of D, L–Lactide in the Melt Imitated with Tetraphenyltin", *Applied Polymer Science*, vol. 29, pp.4265–4277 (1984).

Signhal, et al., "Absorbable Suture Materials: Preparation and Properties", *JMS–Rev. Macomol. Chem. Phys.*, C28 (3&4) pp. 475–502 (1988).

Gilding, et al., "Biodegradable Polymers for use in Surgery–Polyglycolic/Poly(actic) Acid Homo–and Copolymers: 1" *Polymer*, vol. 20, pp. 1459–1464 (Dec. 1979).

Lipinsky et al., "Is Lactic Acid a Commodity Chemical", *Chem. Eng. Progress*, (Aug. 1986).

Gorglewski, et al., "Resorbable Materials of Poly (L–lactide)", *Colloid & Polymer Sci.*, No. 6, pp. 477–484 (1983).

Li et al., "Structure–Property Relationships in the Case of the Degradation of Massive Poly (α–Hydroxy Acids) in Aqueous Media", *Materials Science*, vol. 1, pp. 131–139 (1990).

Barrows, T., "Degradable Implant Materials: A Review of Synthetic Absorbable Polymers and Their Applications" *Clinical Materials*, vol. 1, pp. 233–257 (1986).

Billmeyer, F. *Polymer Science*, Interscience (May, 1965).

*Primary Examiner*—Edward J. Webman
*Attorney, Agent, or Firm*—Hoffmann & Baron

[57] ABSTRACT

Biodegradable controlled release delivery systems using melt-spun biodegradable polymers as carriers for bio-effecting agents such as pharmaceutical actives are disclosed. Oral dosage forms as well as implants are described.

28 Claims, 2 Drawing Sheets

U.S. PATENT DOCUMENTS

| | | | |
|---|---|---|---|
| 3,642,761 | 2/1972 | Ohira | 260/93.7 |
| 3,647,111 | 3/1972 | Stager | 220/83 |
| 3,673,134 | 6/1972 | Anderson | 260/5 |
| 3,676,401 | 7/1972 | Henry | 260/63 |
| 3,679,777 | 7/1972 | Lambert | 260/897 |
| 3,686,000 | 8/1972 | Lawrence | 99/134 |
| 3,707,056 | 12/1972 | Cole | 47/9 |
| 3,723,402 | 3/1973 | Owen | 260/93.7 |
| 3,740,391 | 6/1973 | Williams | 260/233.3 R |
| 3,753,952 | 8/1973 | Gullet | 260/63 R |
| 3,767,638 | 10/1973 | Johnson | 260/93.7 |
| 3,773,919 | 11/1973 | Boswell et al. | 424/19 |
| 3,795,654 | 3/1974 | Kirkpatrick | 260/45.9 |
| 3,797,690 | 3/1974 | Taylor | 220/1 R |
| 3,824,227 | 7/1974 | Rees et al. | 260/112.5 |
| 3,825,624 | 7/1974 | McGaugh | 260/879 |
| 3,825,626 | 7/1974 | McGaugh | 260/897 |
| 3,826,796 | 7/1974 | Sarantekis et al. | 260/112.5 |
| 3,830,764 | 8/1974 | Hudgin | 260/23 H |
| 3,832,312 | 8/1974 | Wright | 260/2.5 HB |
| 3,835,097 | 9/1974 | Fischer | 260/67 FP |
| 3,835,108 | 9/1974 | Immer et al. | 260/112.5 |
| 3,839,297 | 10/1974 | Wasserman et al. | 260/78.3 R |
| 3,839,311 | 10/1974 | Guillory | 260/93.7 |
| 3,840,512 | 10/1974 | Brackman | 260/94.9 GC |
| 3,844,987 | 10/1974 | Clendinning | 260/7.5 |
| 3,846,395 | 11/1974 | Harper | 260/94.9 GC |
| 3,847,852 | 11/1974 | White | 260/23 H |
| 3,850,363 | 11/1974 | Clendinning | 260/7.5 |
| 3,850,855 | 11/1974 | Hirotaka | 260/2 A |
| 3,850,862 | 11/1974 | Clendinning | 260/7.5 |
| 3,852,227 | 12/1974 | Matsuda | 260/23 H |
| 3,853,814 | 12/1974 | Guillet | 260/63 R |
| 3,853,837 | 12/1974 | Fujino et al. | 260/112.5 |
| 3,864,293 | 2/1975 | Miyoshi | 260/23.7 R |
| 3,865,767 | 2/1975 | Boberg | 260/23 H |
| 3,867,324 | 2/1975 | Clendinning | 260/23 H |
| 3,875,300 | 4/1975 | Homm et al. | 424/28 |
| 3,880,952 | 4/1975 | Brackman | 260/878 R |
| 3,882,058 | 5/1975 | Le Brasseur nee Nicourd | 260/23 H |
| 3,886,683 | 6/1975 | Hudgin | 47/9 |
| 3,887,699 | 6/1975 | Yolles | 424/19 |
| 3,888,804 | 6/1975 | Swanholm | 260/2.5 HB |
| 3,892,723 | 7/1975 | McKinley et al. | 260/112.5 |
| 3,896,105 | 7/1975 | Chai et al. | 260/112.5 |
| 3,901,838 | 8/1975 | Clendinning | 260/23 H |
| 3,903,029 | 9/1975 | Young | 260/23 H |
| 3,907,726 | 9/1975 | Tomiyama | 260/17 R |
| 3,917,545 | 11/1975 | Wright | 260/2.5 HB |
| 3,921,333 | 11/1975 | Clendinning | 47/37 |
| 3,923,729 | 12/1975 | Clendinning | 260/40 R |
| 3,923,742 | 12/1975 | Haschke | 260/67 UA |
| 3,925,525 | 12/1975 | LaNieve | 264/40 |
| 3,928,268 | 12/1975 | Sato | 260/23 H |
| 3,929,723 | 12/1975 | Freedman | 260/45.7 S |
| 3,931,068 | 1/1976 | Clendinning | 260/7.5 |
| 3,932,319 | 1/1976 | Clendinning | 260/7.5 |
| 3,932,338 | 1/1976 | Freedman | 260/32.8 A |
| 3,941,759 | 3/1976 | Taylor | 260/92.8 A |
| 3,951,821 | 4/1976 | Davidson | 252/1 |
| 3,954,104 | 5/1976 | Kraskin et al. | 128/263 |
| 3,957,908 | 5/1976 | Heslinga | 260/874 |
| 3,960,150 | 6/1976 | Hussain | 128/260 |
| 3,963,791 | 6/1976 | Guiffre | 260/369 |
| 3,967,623 | 7/1976 | Butterworth et al. | 128/287 |
| 3,968,094 | 7/1976 | Freedman | 526/914 |
| 3,968,095 | 7/1976 | Freedman | 526/914 |
| 3,968,096 | 7/1976 | Freedman | 526/914 |
| 3,972,859 | 8/1976 | Fujino et al. | 260/112.5 LH |
| 3,978,033 | 8/1976 | Gontarz | 526/1 |
| 3,981,303 | 9/1976 | Higuchi et al. | 128/260 |
| 3,981,856 | 9/1976 | Hudgin | 526/4 |
| 3,983,308 | 9/1976 | Palladino | 526/1 |
| 3,986,510 | 10/1976 | Higuchi | 128/260 |
| 3,989,611 | 11/1976 | Shurpik | 204/159.18 |
| 3,991,033 | 11/1976 | Sam | 260/67 FP |
| 3,991,138 | 11/1976 | Tanaka | 260/889 |
| 3,991,766 | 11/1976 | Schmitt et al. | 424/426 |
| 3,992,342 | 11/1976 | Tsubuko et al. | 260/28.5 A |
| 3,993,634 | 11/1976 | Burgaud | 526/4 |
| 3,993,671 | 11/1976 | Huguchi | 128/260 |
| 3,994,855 | 11/1976 | Boberg | 260/42.46 |
| 3,994,869 | 11/1976 | Gontarz | 526/1 |
| 4,000,120 | 12/1976 | Palladino | 526/1 |
| 4,003,846 | 1/1977 | Kuhn et al. | 252/316 |
| 4,008,209 | 2/1977 | Fujino et al. | 260/112.5 LH |
| 4,009,325 | 2/1977 | Freedman | 526/6 |
| 4,010,125 | 3/1977 | Schally et al. | 260/8 |
| 4,010,196 | 3/1977 | Tsuk | 260/484 A |
| 4,011,375 | 3/1977 | Freedman | 526/1 |
| 4,012,565 | 3/1977 | Freedman | 526/6 |
| 4,016,117 | 4/1977 | Griffin | 260/17.4 ST |
| 4,017,469 | 4/1977 | Nicoud espouse la Brassear | 526/19 |
| 4,017,666 | 4/1977 | Freedman | 526/3 |
| 4,017,667 | 4/1977 | Freedman | 526/3 |
| 4,017,668 | 4/1977 | Freedman | 526/6 |
| 4,020,249 | 4/1977 | Freedman | 526/3 |
| 4,021,388 | 5/1977 | Griffin | 260/13 |
| 4,028,480 | 6/1977 | Le Brasseu | 526/3 |
| 4,037,034 | 7/1977 | Plank | 526/5 |
| 4,038,227 | 7/1977 | Swanholm | 260/23 H |
| 4,038,228 | 7/1977 | Taylor | 260/23 AC |
| 4,039,731 | 8/1977 | Freedman | 526/6 |
| 4,042,763 | 8/1977 | Clampitt | 526/4 |
| 4,042,764 | 8/1977 | Gratani | 526/4 |
| 4,042,765 | 8/1977 | Floyd | 526/6 |
| 4,056,499 | 11/1977 | Taylor | 260/23 H |
| 4,056,665 | 11/1977 | Taylor | 526/1 |
| 4,066,568 | 1/1978 | Nakazawa et al. | 252/316 |
| 4,067,836 | 1/1978 | Potts | 260/23 J |
| 4,072,326 | 2/1978 | Groswith | 281/29 |
| 4,073,764 | 2/1978 | Hemmerich | 260/37 N |
| 4,076,798 | 2/1978 | Casey et al. | 424/22 |
| 4,093,709 | 6/1978 | Choi et al. | 424/19 |
| 4,098,728 | 7/1978 | Rosenblatt | 521/141 |
| 4,099,976 | 7/1978 | Kraskin | 106/15 R |
| 4,100,334 | 7/1978 | Palladino | 526/1 |
| 4,101,720 | 7/1978 | Taylor | 526/3 |
| 4,107,071 | 8/1978 | Bayless | 252/316 |
| 4,108,470 | 2/1980 | Collina et al. | 526/64 |
| 4,121,025 | 10/1978 | Scott | 526/4 |
| 4,131,648 | 12/1978 | Choi et al. | 424/22 |
| 4,133,784 | 1/1979 | Otey | 260/17.4 ST |
| 4,136,145 | 1/1979 | Fuchs et al. | 264/164 |
| 4,147,683 | 4/1979 | Vassiliou | 260/29.6 F |
| 4,156,666 | 5/1979 | Odate | 260/23 H |
| 4,166,800 | 9/1979 | Fong | 252/316 |
| 4,177,255 | 12/1979 | Dannelly | 424/21 |
| 4,181,708 | 1/1980 | Dannelly | 424/19 |
| 4,181,709 | 1/1980 | Dannelly | 424/21 |
| 4,181,710 | 1/1980 | Dannelly | 424/33 |
| 4,196,187 | 4/1980 | Dannelly et al. | 424/21 |
| 4,197,375 | 4/1980 | Fox | 525/1 |
| 4,207,221 | 6/1980 | Tobias | 260/28.5 R |
| 4,211,769 | 7/1980 | Okada et al. | 424/177 |
| 4,212,955 | 7/1980 | Tobias | 525/5 |
| 4,215,495 | 8/1980 | Wagner | 37/109 |
| 4,218,350 | 8/1980 | Griffin | 260/17.4 ST |
| 4,218,409 | 8/1980 | Dannelly | 264/4 |
| 4,224,416 | 9/1980 | Taylor | 521/94 |
| 4,234,571 | 11/1980 | Nestor | 424/177 |
| 4,256,785 | 3/1981 | Dannelly | 427/222 |

| | | | |
|---|---|---|---|
| 4,256,851 | 3/1981 | Taylor | 525/1 |
| 4,293,539 | 10/1981 | Ludwig et al. | 424/19 |
| 4,318,905 | 3/1982 | Nestor et al. | 424/177 |
| 4,337,181 | 6/1982 | Otey | 523/128 |
| 4,341,767 | 7/1982 | Nestor et al. | 424/177 |
| 4,360,606 | 11/1982 | Tobias | 523/124 |
| 4,371,516 | 2/1983 | Gregory et al. | 424/22 |
| 4,374,938 | 2/1983 | Verheist | 523/124 |
| 4,376,743 | 3/1983 | Dees | 264/103 |
| 4,426,500 | 1/1984 | Johnson | 525/537 |
| 4,439,199 | 3/1984 | Amkraut et al. | 604/894 |
| 4,451,589 | 5/1984 | Morman | 523/124 |
| 4,461,853 | 7/1984 | Gilead | 523/126 |
| 4,469,613 | 9/1984 | Munteann et al. | 252/92 |
| 4,471,077 | 9/1984 | Lange | 521/64 |
| 4,476,255 | 10/1984 | Bailey | 523/125 |
| 4,490,291 | 12/1984 | Fujino | 260/112.5 LH |
| 4,492,685 | 1/1985 | Keith et al. | 424/28 |
| 4,495,311 | 1/1985 | Hudgin | 523/126 |
| 4,495,315 | 1/1985 | Miyoshi | 523/125 |
| 4,496,592 | 1/1985 | Kuwahara et al. | 426/5 |
| 4,499,223 | 2/1985 | Yamamori | 524/176 |
| 4,500,546 | 2/1985 | Turbak et al. | 514/781 |
| 4,517,318 | 5/1985 | Miyoshi | 523/126 |
| 4,526,938 | 7/1985 | Churchill | 525/415 |
| 4,530,840 | 7/1985 | Tice et al. | 514/179 |
| 4,542,025 | 9/1985 | Tice et al. | 424/78 |
| 4,585,797 | 4/1986 | Cioca | 514/773 |
| 4,595,584 | 6/1986 | Wu et al. | 424/19 |
| 4,634,720 | 1/1987 | Dorman et al. | 521/63 |
| 4,637,931 | 1/1987 | Schmitz | 424/78 |
| 4,645,664 | 2/1987 | Lange | 424/78 |
| 4,675,189 | 6/1987 | Kent et al. | 424/490 |
| 4,677,177 | 6/1987 | Shibanai | 527/300 |
| 4,686,790 | 8/1987 | Lahalih | 47/9 |
| 4,687,676 | 8/1987 | Wu et al. | 427/3 |
| 4,717,567 | 1/1988 | Wu et al. | 424/462 |
| 4,719,246 | 1/1988 | Murdoch et al. | 521/134 |
| 4,757,128 | 7/1988 | Domb et al. | 528/271 |
| 4,779,806 | 12/1988 | Langer et al. | 241/1 |
| 4,780,319 | 10/1988 | Zentner | 424/476 |
| 4,789,724 | 12/1988 | Domb et al. | 528/176 |
| 4,839,450 | 6/1989 | Fanta | 527/313 |
| 4,855,326 | 8/1989 | Fuisz | 514/777 |
| 4,857,311 | 8/1989 | Domb et al. | 424/78 |
| 4,861,627 | 8/1989 | Mathiowitz et al. | 427/213.31 |
| 4,873,085 | 10/1989 | Fuisz | 424/400 |
| 4,873,270 | 10/1989 | Aime et al. | 523/128 |
| 4,886,870 | 12/1989 | D'Amore et al. | 528/206 |
| 4,888,176 | 12/1989 | Langer et al. | 424/426 |
| 4,888,857 | 12/1989 | Pinto et al. | 19/80 R |
| 4,889,119 | 12/1989 | Jamiolkowski et al. | 606/220 |
| 4,891,225 | 1/1989 | Langer et al. | 424/428 |
| 4,891,404 | 1/1990 | Narayan et al. | 525/54.2 |
| 4,898,734 | 2/1990 | Mathiowitz et al. | 424/426 |
| 4,906,474 | 3/1990 | Langer et al. | 424/428 |
| 4,931,488 | 6/1990 | Chiquet | 523/126 |
| 4,933,431 | 6/1990 | Domb et al. | 528/328 |
| 4,939,194 | 7/1990 | Scott | 524/134 |
| 4,946,929 | 8/1990 | D'Amore et al. | 528/206 |
| 4,948,820 | 8/1990 | Addeo | 523/124 |
| 4,952,665 | 8/1990 | Seelmann-Eggebert | 526/318.4 |
| 4,983,645 | 1/1991 | Schwab | 522/47 |
| 4,985,251 | 1/1991 | Levy | 424/404 |
| 4,997,856 | 3/1991 | Fuisz | 514/777 |
| 4,997,904 | 3/1991 | Domb et al. | 528/206 |
| 4,999,417 | 3/1991 | Domb et al. | 528/271 |
| 5,010,167 | 4/1991 | Ron et al. | 528/328 |
| 5,011,532 | 4/1991 | Fuisz | 106/215 |
| 5,015,293 | 5/1991 | Mayer | 106/162 |
| 5,028,632 | 7/1991 | Fuisz | 514/772 |
| 5,034,421 | 7/1991 | Fuisz | 514/772 |
| 5,070,122 | 12/1991 | Vanderbilt | 524/47 |
| 5,096,492 | 3/1992 | Fuisz | 106/215 |

FIG. 2

BIODEGRADABLE CONTROLLED RELEASE FLASH FLOW MELT-SPUN DELIVERY SYSTEM

BACKGROUND OF THE INVENTION

The present invention relates to a new controlled release delivery system using melt spun biodegradable polymers as a carrier or host material for a bio-effecting agent such as a pharmaceutical active or a hormonal compound.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of controlled or sustained release dosage forms are well known. Among the most important advantages are: (1) increased contact time for the drug to allow for local activity in the stomach, intestine or other locus of activity; (2) increased and more efficient absorption for drugs which have specific absorption sites; (3) the ability to reduce the number of dosages per period of time; (4) employment of less total drug; (5) minimization or elimination of local and/or systemic side effects; (6) minimization of drug accumulation associated with chronic dosage; (7) improved efficiency and safety of treatment; (8) reduced fluctuation of drug level; and (9) better patient compliance with overall disease management.

Additionally, many experts believe sustained release drug delivery has many important non-therapeutic ramifications as well, including a financial saving to the patient in terms of less lost work days, less hospitalization and fewer visits to the physician.

It is known that certain design parameters are critical to proper drug delivery. Typically, they are: (1) delivering the drug to the target tissue; (2) supplying the drug in the correct temporal pattern for a predetermined period of time and (3) fabricating a delivery system that provides drug in the desired spatial and temporal pattern. Controlled or sustained release drug delivery systems are intended to manipulate these parameters to achieve the aforementioned advantages when compared to conventional pharmaceutical dosing.

Controlled release of actives has conventionally focused on oral dosage forms such as tablets and capsules, where release of the active was accomplished by diffusion through or erosion of the matrix. Conventional formulations use waxes or hydrophilic gums as the primary drug carriers to prolong the release of the active. In wax formulations, the drug is dispersed in the wax matrix in a molten state. This method has the disadvantage of possible decomposition and/or crystalline formation of the drug, rendering it less active or effective as a therapeutic agent. Other systems using polymeric coatings or laminates on the tablets to delay tablet disintegration and protect the active from prematurely releasing in the stomach where gastric secretions would destroy its activity. Still other systems use water-swellable hydrogel matrices to control the release of the agent by surface-to-center swelling of the matrix and subsequent diffusion of the agent. For common methods of producing controlled release products, see *Sustained And Controlled Release Drug Delivery Systems,* Robinson, Joseph R., Ed. pp 138–171, 1978, Marcel Dekker, Inc. N.Y., N.Y.

More recently, the use of biodegradable polymers as matrices or carriers for drugs has become more prevalent. For example, the use of biodegradable articles, such as dispensing vehicles, which are implanted in the animal, are intended to be broken down or degraded by the animal body into residues or moieties which are absorbed, metabolized or otherwise naturally removed by the body. Early forms of these implantable polymeric devices are exemplified in U.S. Pat. No. 3,882,699, which discloses a drug dispersed in a biodegradable polymeric material and shaped into a solid shape. This patent requires the use of low crystalline lactic acid polymers in order to obtain faster release of drug. Solvents are used to form homogeneous solutions of the drug/polymer mixture and extrusion, molding or compaction techniques are used to form the product.

Numerous drug delivery systems using polymers which are bio-eroding in the body are disclosed. For example, U.S. Pat. Nos. 4,888,176, 4,891,225, 4,757,128, 4,093,709 disclose the use of polyanhydrides, poly(othoesters) and poly(orthocarbonates) to make articles for delivering agents. These patents and others deal with biodegradable synthetic polymers as drug matrices for controlled release of the drug over a sustained period of time. These delivery systems are manufactured using conventional solvent casting, extrusion or molding techniques to physically entrap the drug in the polymer matrix. Solvent casting involves preparing a solution of drug and polymer using a solvent and removing the solvent to leave a residue of polymer and drug presumably in intimate physical contact. The residue can then be further processed or shaped using conventional thermoplastic processing methods.

Another conventional thermoplastic processing technique involves the use of melt-spinning techniques. For example, U.S. Pat. No 4,335,232 to Irwin discloses melt-spinning aromatic copolyesters; and U.S. Pat. No. 4,072,658 to Okamato, et al. discloses melt-spinning of polystyrene. These conventional melt-spinning techniques involve subjecting a feedstock to sustained heat treatment and are described in F. Billmeyer, Jr., *Textbook Of Polymer Science,* 518–522 (Wiley International Edition 2d). Conventional spinning processes require melting the polymer or dissolving the polymer in solution (an exception is the aqueous dispersion of a polymer, such as polytetrafluoroethylene), followed by removal of the liquid and sintering. In these melt-spinning procedures, molten polymer is pumped at a constant rate under high pressure through a plate having a number of small holes, which is referred to as a spinneret. Polymer is melted, usually by contacting it with a hot grid or by use of an extrusion-type screw, and passed directly to a meter pump. Filaments emerge from the spinnaret into air where it begins to cool. As the fibers solidify, they are brought together and drawn to orient the fibers. In both dry spinning and wet spinning procedures, the polymer or polymer derivative is put into solution prior to forming the fiber.

All of the conventional thermoplastic processing techniques when applied to drugs and other active agents suffer from a number of obvious drawbacks. Processing temperatures encountered in the polymeric melt stage vary with the type of polymer and are often too high to retain stability of the drug. Drug/polymer interactions or degradation of the drug may occur, rendering the drug inactive or less effective for its intended purpose. Biodegradable polymers such as polyanhydrides require higher molecular weights in order to avoid brittleness during solvent casting and maintain their structural integrity in the resultant products.

The literature discloses that release of drugs from polymer systems is dependent upon a number of factors. One critical factor is the degree of crystallinity present in the polymer. The higher the degree of crystallinity, the slower the rate of degradation of the polymer and thus the slower the release of drug or active from the polymer matrix. Conversely, polymers with less crystallinity generally degrade more easily or rapidly, thereby effectuating release of the active in a shorter time. For a discussion of the effect of polymer crystallinity on drug release see "Using Biodegradable Polymers In Advanced Drug Delivery Systems", Schacht, Etiens 41, *Medical Device Technology*, January–February 1990; and Flory, Paul J., *Principles Of Polymer Chemistry*, 5th Ed., 1966. The concern regarding crystallinity has been addressed by attempting to balance the molecular weight of the polymer with its crystalline structure to obtain the desired release rate and duration. The conventional processing techniques have not afforded practical, reproducable and cost effective methods for solving this concern.

More recently, a new method of producing substances having pharmacological properties was disclosed in U.S. Pat. No. 4,855,326. This patent discloses combining sugar with a medicament and spinning the combination into a readily water-soluble floss or fiber. In U.S. Pat. No. 5,011,532, the disclosure deals with oleaginous substances such as vegetable oil, baby oil, margarine, lanolin, cocoa butter and the like, and how their lack of affinity for water is altered by mixing the oleaginous substance with sugar and melt-spinning the mixture in cotton candy spinning machines or the equivalent. As so modified, the products disperse in water forming a colloidal or pseudocolloidal dispersion.

Other disclosures which relate to spinning substances with one or more sugars are found in U.S. Pat. No. 4,873,085 issued Oct. 10, 1989, U.S. Pat. No. 5,034,421 issued Jul. 23, 1991, U.S. Pat. No. 5,028,632 issued Jul. 2, 1991, and U.S. Pat. No. 4,997,856 issued Mar. 5, 1991. The products described in the above-mentioned patents and applications are all produced by processing in a cotton candy machine. Illustrative of a cotton candy machine is the Econo Floss Model 3017 manufactured by Gold Medal Products Co. of Cincinnati, Ohio. The process described in the above-identified disclosures involve the use of sugar(s) as a feedstock material which is spun to produce a material such as a floss, fiber, and the like. Accordingly, the technology described in the above-identified disclosures relies on the physical characteristics of sugar.

It is apparent that a need exists for a controlled release composition for delivering bio-effecting actives such as therapeutic and prophylactic agents to animals which are based on biodegradable non-saccharide polymer carriers which can be made without the disadvantages associated with conventional thermoplastic processing and which are capable of controllably releasing the active over a predetermined period of time at a chosen rate. The present invention provides such a composition, and offers an efficient and cost effective method of preparation.

SUMMARY OF THE INVENTION

The present invention relates to unique controlled release compositions and their methods of preparation. More particularly, the present invention relates to biodegradable controlled release compositions formed by melt-spinning a non-saccharide biodegradable polymer and a bio-effecting agent.

For purposes of this invention, the following definitions shall apply:

The term "biodegradable" shall mean the ability to be degraded by processes involving biological conditions, such as those present in the bodies of humans or other animals. More specifically, this term indicates the physical or chemical breaking down of the polymer into smaller units which are preferably innocuous, non-toxic and are readily eliminated or metabolized by the body. The term includes the concepts of erosion and diffusion. Erosion is generally classified either as heterogeneous or homogeneous. The former refers to surface erosion of the polymer matrix containing the active, and the latter refers to erosion beneath the surface into the body of the matrix containing the active. Biodegradation is the principle allowing for release of the active material and absorption of the degradation products. A number of factors play a role in biodegradation and hence in controlling release including, the nature of the polymer, the type of active, the geometry and surface area of the product, the ratio of matrix or carrier to active, the degree of polymer crystallinity, the process of preparing the active/polymer mixture, to name a few. It is preferred that the inventive compositions perform in response to self-regulated feedback mechanisms in the body. Fluids in the body are the source of components which attack the polymer, allowing for erosion of the carrier material and release of the active. Such factors as hydrolysis, pH, enzymes, bile fluids and mechanical forces present in the body may contribute to biodegradation. Thus, for a given application the type of polymer chosen can be tailored to fit those factors present at the site of delivery. For example, pH-sensitive polymers may be chosen if the purpose is to bypass release in the stomach and deliver sustained levels in the small intestine. On the other hand, if the composition is to be implanted in the body, such as in a closed wound, the polymer should be sufficiently stable without hydrolysis of the polymer for a desired period.

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated.

The term "bio-effecting active" includes therapeutic agents such as pharmaceutical or pharmacological active agents, e.g., drugs and medicaments, as well as prophylactic agents, diagnostic agents and other chemicals or materials useful in treating or preventing conditions, infections and disease found in animals. The compositions of the present invention are particularly effective in humans and other mammals, but are intended for use in other animals such as fish and birds, or plants, insects and other organisms.

Both water-soluble and water-insoluble drugs have been found to be useful in the delivery systems covered by the invention. For purposes of this application, the terms water-soluble and water-insoluble drug will have the following definitions. Water-soluble drug will mean that up to 30 parts of solvent are required to completely dissolve 1 part of drug. The term water-insoluble drug will mean greater than 30 parts of solvent are required to dissolve 1 part of the drug. For further discussion of these terms, see USP XXII, page 1807 incorporated herein by reference. The compositions can be used to obtain specific controlled release profiles, combining aspects of immediate release, intermediate release, and sustained release in one formulation.

The term "melt-spinning" has been used in the claims. However, in the context of the present invention "melt-spinning" means subjecting solid feedstock i.e. biodegradable polymer/bio-effecting active combinations to the combination of temperature, thermal gradients, mechanical forces, flow, and flow rates during processing which is comparable to that applied to the feedstock during operation of a machine for producing cotton candy. This is in contrast to the use of the term melt-spinning in the polymer-processing art. Conventional "melt-spinning" is used by the polymer technician to describe processes for extruding polymers which are held under liquid or melted conditions for comparatively long periods of time before being extruded under direct pressure through an orifice.

"Flash flow" is referred to in the present process as a phenomena which occurs when a solid carrier material (e.g., thermoplastic material) is subjected to conditions of temperature and shear sufficient to provide internal flow at a subparticle level. This condition produces a transformation of physical and/or chemical structure without degradation of the material. Internal flow occurs when the infrastructure of the material breaks down sufficiently to permit movement of the material at a subparticle level, and probably at a molecular level. At a molecular level, internal flow contemplates the movement of molecules relative to each other.

In the present invention, thermoplastic material is subjected to flash flow sufficiently to deform and pass through an opening under minimum amount of force. The force used in the present preferred embodiments of the invention is centrifugal force provided by a spinning head from which the deformed flowable material is thrown at high speed. No external force is imposed on the flowable thermoplastic material after it is flung out of the spinning head. The thermoplastic material instantaneously reforms as a solid having altered physical and/or chemical structure. The altered structure results from the forces acting on the material as it exits the head and is hurled outwardly during the brief period during which it experiences flash flow.

The flash flow phenomena of the present invention occurs in not more than one second, preferably on the order of tenth of seconds, e.g., not more than about 0.4 seconds, and most preferably on the order of milliseconds and certainly not more than 0.1 seconds. This unique phenomena can be produced by relatively high speed distribution of the thermoplastic material to an environment of elevated temperature under a constant force, such as centrifugal force, caused by high speed rotation of a continuous-wall spinning head. One example of a mechanism for producing such a combination is a cotton candy making machine. Variations of such an apparatus are contemplated for use in the present invention. The important aspect is that the flash flow phenomena be induced in a solid feedstock for rapid transition to solid thermoplastic material having an altered structure from that of the feedstock.

Those polymers useful as carrier materials for the bio-affecting actives include non-saccharide polymers and copolymers which are substantially biocompatible and biodegradable. Mixtures of polymers as well as layers of polymers are contemplated. The polymers must be capable of undergoing melt-spin processing as defined herein. These polymers should have a balance of hydrophobic/hydrophilic characteristics to resist attack by body fluids, e.g., hydrolysis, for a desired time, yet be degradable to allow for controlled release. Biocompatability, low toxicity and a high degree of amorphous characteristics are important. In applications involving tissue implants, a low glass transition temperature is desirable for pliability and comfort. Hydrolytic labile backbone or side chains contribute to the degradative process.

The present invention also relates to unique methods of preparing controlled release melt-spun delivery systems for actives including subjecting a biodegradable non-saccharide polymeric carrier and a bio-affecting active to melt-spinning to unite said polymer and active under conditions which produce a solid capable of releasing said active under conditions found in the body of an animal. A method of treatment for diseases and other conditions found in the body is also disclosed. Such a treatment involves the administration of an effective amount of a biodegradable controlled release composition comprising a non-saccharide biodegradable polymeric carrier and a bio-effecting therapeutic or prophylactic agent. The present invention also relates to novel solid sustained released delivery systems and products made therefrom obtained by subjecting a biodegradable spinnable non-saccharide host polymer and a guest bio-effecting active to flash flow processing.

DETAILED DESCRIPTION OF THE INVENTION

Those polymers which are useful in the present invention include any melt-spinnable thermoplastic polymers which are capable of biodegrading under conditions found in the body of animals. As previously described, the polymers should be capable of being melt-spun as defined herein. The melting points and glass transition temperatures of these polymers may vary widely, as will their molecular weights. The speed, temperature and time of the melt-spinning apparatus can be adjusted accordingly to accomodate these property variations and produce a product useful for controlled release. The polymer must therefore be capable of undergoing flash flow as described herein.

Once a polymer/bio-effecting active combination has been spun, it may take a number of solid or solid-like forms such as flakes, chips, floss, fibers, ribbons and the like. These product forms can be used in that form or further modified into other delivery forms for specific application.

It is to be understood that any biodegradable thermoplastic polymer that can be subjected to melt-spinning as defined herein without being degraded, burnt or otherwise damaged, can be used as the carrier for the bio-effecting active. Melt-spinning a mixture of such polymer and active produces a trapped form of said active agent which isolates the active agent from its surroundings yet permits slow release in the appropriate fluid environment. The principal limitation upon carrier or active is that neither be degraded or rendered substantially inactive while being melt-spun. Also, the polymer carrier and active agent should be chemically compatible.

Useful polymeric materials include polymers, copolymers, block polymers and mixtures thereof. Among the known useful polymers or polymer classes which meet the above criteria are: poly(glycolic acid) (PGA), poly(lactic acid) (PLA), polydioxanes, polyoxalates, poly($\alpha$-esters), polyanhydrides, polyacetates, polycaprolactones, poly(orthoesters), polyamino acids, polyurethanes, polycarbonates, polyiminocarbonates, polyamides, poly(alkyl cyanoacrylates), and mixtures and copolymers thereof. Additional useful polymers include, stereopolymers of L- and D-lactic acid, copolymers of bis(p-carboxyphenoxy) proprionic acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of $\alpha$-amino acids, copolymers of $\alpha$-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/ glycolide polymer" containing "propanoic acid, 2-hydroxy-polymer with hydroxyacetic acid." Four such polymers include Medisorb 100 L believed to be 100% lactide having a melting point within the range of 338°–347° F. (170°–175° C.); Medisorb 100 PGA, believed to be 100% glycolide having a melting point within the range of 437°–455° F. (225°–235° C.); Medisorb 8515 DL, believed to be 85% lactide and 15% glycolide; and Medisorb 5050 DL, believed to be a copolymer of 50% lactide and 50% glycolide.

The Biodel materials represent a family of various polyanhydrides which differ chemically.

Certain polymers exhibit particularly useful permeation rates for specific drugs. For example, polycaprolactones are known to have high permeation rates to steroids such as testosterone, progesterone and norgestral. Thus, a particular polymer can be chosen for its ability to release certain drugs in a particular release profile.

The bio-affecting active may be selected from any suitable drug, therapeutic or prophylatic agent which can be melt-spun with a selected polymer without losing substantial activity for the chosen therapy. A broad range of materials are therefore useful and but for the limitations discussed above, the invention contemplates the classes of water-soluble and water-insoluble actives. Representative non-limiting classes of drugs useful include those falling into the following therapeutic categories: ace-inhibitors; anti-anginal drugs; anti-arrhythmias; anti-asthmatics; anti-cholesterolemics; anti-covulsants; anti-depressants; anti-diarrhea preparations; anti-histamines; anti-hypertensive drugs; anti-infectives; anti-inflamatory agents; anti-lipid agents; anti-manics; anti-nauseants; anti-stroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; antiarthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migrain treatments; mineral supplements; mucolytics; narcotics; neuroleptics; neuromuscular drugs; NSAIDS; nutritional additives; peripheral vaso-dilators; polypeptides; prostaglandins; psychotropics; renin inhibitors; respiratory stimulants; steroids; stimulants; sympatholytics; thyroid preparations; tranquilizers; uterine relaxants; vaginal preparations; vaso-constrictors; vaso-dilators; vertigo agents; vitamins; wound healing agents.

Non-limiting examples of specific bio-effecting agents which may be useful in the present invention can be chosen from the list which follows; Mixtures of these agents and their salts used for appropriate therapies are also contemplated: acetaminophen; acetic acid; acetylsalicylic acid and its buffered form; albuterol and its sulfate; alcohol; alkaline phosphatase; allantoin; aloe; aluminum acetate, carbonate, chlorohydrate, hydroxide; alprozolam; amino acids; aminobenzoic acid; amoxicillin; ampicillin; amsacrine; amsalog; anethole; ascorbic acid; aspartame; atenolol; bacitracin; balsam peru; BCNU (carmustine) beclomethasone dipropionate; benzocaine; benzoic acid; benzophenones; benzoyl peroxide; bethanechol; biotin; bisacodyl; bornyl acetate; bromopheniramine maleate; buspirone; caffeine; calamine; calcium, calcium carbonate, casinate and hydroxide; camphor; captopril; cascara sagrada; castor oil; cefaclor; cefadroxil; cephalexin; cetylalcohol; cetylpyridinium chloride; chelated minerals; chloramphenicol; chlorcyclizine hydrochloride; chlorhexidine gluconate; chloroxylenol; chloropentostatin; chlorpheniramine maleate; cholestyramine resin; choline bitartrate; chondrogenic stimulating protein; cimetidine hydrochloride; cinnamedrine hydrochloride; citalopram; citric acid; cocoa butter; cod liver oil; codeine and codeine phosphate; clonidine and its hydrochloride salt; clorfibrate; cortisone acetate; ciprofloxacin HCl; cyanocobalamin; cyclizine hydrochloride; danthron; dexbrompheniranime maleate; dextromethorphan hydrobromide; diazapam; dibucaine; diclofenac sodium; digoxin; diltiazem; dimethicone; dioxybenzone; diphenhydramine citrate; diphenhydramine hydrochloride; docusate calicum, potassium and sodium; doxycycline hyclate; doxylamine succinate; efaroxan; enalapril; enoxacin; erythromycin; estropipate; ethinyl estradiol; ephedrine; epinephrine bitartrate; erythropoietin; eucalyptol; ferrous fumarate, gluconate and sulfate; folic acid; fosphenytoin; 5-fluorouracil (5-FU) fluoxetine HCl; furosemide; gabapentan; gentamicin; gemfibrozil; glipizide; glycerin; glyceryl stearate; griseofulvin; growth hormone; guaifenesin; hexylresorcinol; hydrochlorothiaxide; hydrocodone bitartrate; hydrocortisone and its acetate; 8-hydroxyquinoline sulfate; ibuprofen; indomethacin; inositol; insulin; iodine; ipecac; iron; isoxicam; ketamine; koalin; lactic acid; lanolin; lecithin; leuprolide acetate; lidocaine and its hydrochloride salt; lifinopril; liotrix; lovastatin; luteinizing hormone; LHRH (luteinizing hormone releasing hormone); magnesium carbonate, hydroxide, salicylate, trisilocate; mefenamic acid; meclofenanic acid; meclofenamate sodium; medroxyprogesterone acetate; methenamine mandelate; menthol; meperidine hydrochloride; metaproterenol sulfate; methyl nicotinate; methyl salicylate; methylcellulose; methsuximide; metronidazole and its hydrochloride; metoprolol tartrate; miconazole nitrate; mineral oil; minoxidil; morphine; naproxen and its sodium salt; nifedipine; neomycin sulfate; niacin; niacinamide; nicotine; nicotinamide; nitroglycerin; nonoxynol-9; norethindone and its acetate; nystatin; octoxynol; octoxynol 9; octyl dimethyl PABA; octyl methoxycinnamate; omega-3 polyunsaturated fatty acids; omeprazole; oxolinic acid; oxybenzone; oxtriphylline; para-aminobenzoic acid (PABA); padimate O; paramethadione; pentastatin; peppermint oil; pentaerythriol tetranitrate; pentobarbital sodium; pheniramine maleate; phenobarbital; phenol; phenolphthalein; phenylephrine hydrochloride; phenylpropanolamine and its hydrochloride salt; phenytoin; phenelzine sulfate; pirmenol; piroxicam; polymycin B sulfate; potassium chloride and nitrate; prazepam; procainamide hydrochloride; procaterol; propoxyphene and its HCl salt; propoxyphene napsylate; pramiracetin; pramoxine and its hydrochloride salt; propronolol HCl; pseudoephedrine hydrochloride and sulfate; pyridoxine; quinapril; quinidine gluconate and sulfate; quinestrol; ralitoline; ranitadine; resorcinol; riboflavin; salicylic acid; sesame oil; shark liver oil; simethicone; sodium bicarbonate, citrate and fluoride; sodium monofluorophosphate; sucralfate; sulfanethoxazole; sulfasalazine; sulfur; tacrine and its HCl salt; theophylline; terfenidine; thioperidone; trimetrexate; triazolam; timolol maleate; tretinoin; tetracycline hydrochloride; tolmetin; tolnaftate; triclosan; triprolidine hydrochloride; undecylenic acid; vancomycin; verapamil HCl; vidaribine phosphate; vitamins A, B, C, D, $B_1$, $B_2$, $B_6$, B12, E, K; witch hazel; xylometazoline hydrochloride; zinc; zinc sulfate; zinc undecylenate.

Drugs which are chemically linked to the polymer, e.g. macromolecular prodrugs are contemplated.

Useful dosage forms include without limitation oral forms such as tablets, capsules, beads, granules, aggregates, syrups, powders, gels, solids, semi-solids, suspensions and liquids. Injectable forms, lotions, transdermal delivery systems including dermal patches, implantable forms or devices, aerosols or nasal mists, suppositories, salves and ointments are also useful.

The inventive compositions have great versatility in their application. Of particular utility however, is the administration of bio-effecting agent to site-specific localities. For example, the controlled release compositions of the present invention can be used as the suture or component of a suture, i.e. threads of a multi-filament suture, for wounds. There compositions can be used in steri-strip wound closure materials such as dressings and the like. The compositions can be used for wound management such as by direct application to burns, abrasions, skin diseases or infections and the like. Other uses such as packing agents for nasal wounds or other open wounds are also contemplated. The packing agents can, for example, also contain blood clotting factors such as proconvertin, plasma thromboplastin, Stuart factor, Vitamin K, fibrinogen, drugs such as phytonadione or hormones such as estrogen.

In certain preferred embodiments, a growth regulator, such as a human somatatropin, a bovine somatatropin or a porcine somatatropin, is incorporated in the non-saccharide polymer. The biodegradable polymers which are melt-spun together with human somatatropin can be effectively used in tissue cultures to promote growth of human tissue. The growth of cells from fetal tissue or foreskin tissue can be stimulated by the gradual release of the hormone from the biodegradable polymer. The biodegradable polymer containing the growth hormone can be in the form of fibers or it can be material obtained by placing a support close to the spinning head to collect the material on the support while it is still in its flowable state. Where a support is coated with such biodegradable polymer containing the hormone, the cells to be grown can be placed over the coated support to form tissue segments or patches which can be used for skin grafts and the like. Cartilage tissues can also be grown by similar procedures.

In applications involving treatment of ruminants, if the dosage form is to be administered orally, the polymer must provide a protective barrier against the fluids of the rumen and allow for passage to the abomasum where polymeric degradation and concomitant release of active can occur over time. This generally means that the polymeric matrix or carrier is designed to be resistant to pH>5 but slowly degraded at pH<3.5.

In the case of oral administration of actives, such as insulin, which are destroyed in gastric juices, the polymer must provide a similar protective and delivery function. Of course, alternatives to oral administration include biodegradable implants which are designed to deliver the appropriate therapeutic dose for the specific condition treated.

A variety of additives can be incorporated into the inventive compositions for their intended functions. Their additives are generally added in minor amounts. Examples of classes of additives include excipients, lubricants, buffering agents, disintegrating agents, stabilizers, foaming agents, pigments, coloring agents, fillers, bulking agents, sweetening agents, flavoring agents, fragrances, release modifiers, adjuvants, plasticizers, flow accelerators, polyols, granulating agents, diluents, binders, buffers, absorbents, glidants, adhesives, antiadherents, acidulants, softeners, resins, demulcents, solvents, surfactants, emulsifiers, elastomers and mixtures thereof.

Useful additives include, for example, gelatin, vegetable proteins such as sunflower protein, soybean proteins, cotton seed proteins, peanut proteins, rape seed proteins, blood proteins, egg proteins, acrylated proteins; water-soluble polysaccharides such as alginates, carrageenans, guar gum, agar-agar, gum arabic and related gums (gum ghatti, gum karaya, gum tragacanth), pectin; water-soluble derivatives of cellulose: alkylcelluloses, hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxbutylmethylcellulose, cellulose esters and hydroxyalkylcellulose esters such as: cellulose acetate phthalate (CAP), carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVP/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; and other similar polymers.

Processing aids such as mono- and triglycerides are useful as well. In certain preferred embodiments, saccharides such as sucrose, maltodextrin, polydextrose, lactose, maltose and the like are added to the non-saccharide polymer in amounts of about 1 to about 35% by weight of the non-saccharide polymer. The bioeffecting agent is mixed with the saccharide before spinning and in certain embodiments can be present in both the saccharide material and the non-saccharide carrier. Upon spinning, the saccharide tends to form pockets or cavities within the non-saccharide polymer which results in a material where the bioeffecting agent is released in accordance with diffusion gradients from the relatively soluble saccharides and in accordance with the degradation properties of the non-saccharide polymer when the bioactive compound is incorporated in such polymer.

Further additives may be inorganic fillers, such as the oxides of magnesium, aluminum, silicon, titanium, and the like preferably in a concentration range of about 0.02 to about 3% by weight and preferably about 0.02 to about 1% based on the weight of all components.

Further examples of additives are plasticizers which include polyalkylene oxides, such as polyethylene glycols, polypropylene glycols, polyethylene-propylene glycols; organic plasticizers with low molecular weights, such as glycerol, glycerol monoacetate, diacetate or triacetate; propylene glycol, sorbitol, sodium diethylsulfosuccinate, triethyl citrate, tributyl citrate, and the like.

Examples of coloring agents include known azo dyes, organic or inorganic pigments, or coloring agents of natural origin. Inorganic pigments are preferred, such as the oxides of iron or titanium.

One particularly useful class of additives which can be incorporated into the spun matrix of the present compositions include radio opaque materials. These materials can be used to monitor the position of the controlled release composition via x-rays, and in cases where non-biodegradable material is present, such as carbon fibers, these will remain in the body subsequent to degradation of the polymer as a marker to show the site of the wound or the cite of treatment.

Prior to forming the polymer and drug mixture, the polymers were cryoground to reduce the particle size and facilitate spinning. Cryogrinding was conducted under liquid nitrogen in a RETSCH Model ZM-1 Ultra Centrifugal Mill, 2.0 mm sieve with 12 tooth rotor.

The amount of bio-effecting active present is dependent upon the treatment indicated. The bio-effecting/polymer ratios will vary accordingly. In general, however, the polymer is present in amounts of about 50 to 99% by weight and preferably about 75 to 90%. The balance of the composition is active, with various amounts of additives as previously mentioned.

pestle. The biodegradable polymer was then slowly added with continuous mixing. The mixtures were preferably homogeneous.

Each of the example mixtures were spun on an Econo Floss spinning machine which was modified to provide for variable temperature of the heating ribbon and variable speed of the rotating head. The spinning head was 5.5 inches in diameter having slits in the outer containment band which were 3–5 mm long by 0.5–0.75 mm wide. Where a Kapton® liner is specified, it is a band of Kapton® polymer (polyimide available from DuPont) material inserted between the heating element and the outer containment band with 0.042" holes in the Kapton® band aligned with the slits in the outer containment band.

Table I also indicates the relative weight percents of the melt-spun components as well as the rotational speed (RPM) and temperature of the spinning head.

TABLE I

| Example | Active/% wt | Polymer/% wt | Processing aid/% wt | RPM | Temp. °C. | Kapton*** Liner |
|---|---|---|---|---|---|---|
| 1 | Vancomycin/11% | *polyglyocolide/80% | **MCT/9% | 4,500 | 140 | YES |
| 2 | Tolmetin NA/9% | polyglyocolide/82% | MCT/9% | 3,600 | 140 | NO |
| 3 | Gentamicin/9% | polyglyocolide/82% | MCT/9% | 3,600 | 140 | NO |
| 4 | Ibuprofen/5% Diphenhydramine/5% | polyglyocolide/81% | MCT/9% | 4,500 | 150 | YES |
| 5 | Vancomycin/9% | (a) PDS/82% | MCT/9% | 3,600 | 140 | NO |
| 6 | Toluetin NA/9% | PDS/82% | MCT/9% | 3,600 | 140 | NO |
| 7 | Gentamicin/9% | PDS/82% | MCT/9% | 3,600 | 140 | NO |
| 8 | Tolmetin NA/9% | polyglyocolide(41%)/ PDS(41%) copolymer/80% | MCT/9% | 3,600 | 140 | NO |
| 9 | Gentamicin/17% | (b) P(SA)/74% | MCT/9% | 4,500 | 120 | YES |
| 10 | Vancomycin/17% | P(SA)/74% | MCT/9% | 4,500 | 120 | YES |
| 11 | — | P(SA)/91% | MCT/9% | 4,500 | 120 | NO |
| 12 | Insulin/5% | (c) P(CPL)/95% | — | 3,600 | 135 | NO |
| 13 | Insulin/5% | P(CPL)70% Sucrose/25% | — | 3,600 | 135 | NO |
| 14 | Vancomycin/10% | (d) poly L-lactic acid/82% | MCT/9% | 3,600 | 135 | NO |
| 15 | Gentamicin/10% | (e) poly L-lactic acid/82% | MCT/9% | 3,600 | 135 | NO |

*Copolymer of L(-) lactide (69.29%) and glycolide (30.05%)
**MCT = medium chain triglyceride (miglycol 812, Huls America)
***Kapton liner with three 0.04211 holes per containment band slot
(a) PDS = poly-para-dioxane polymer
(b) P(SA) = polysabacic acid polymer
(c) P(CPL) = polycaprolactone polymer
(d) MW 40-100M (Medisorb 100DL available from Medisorb International L.P.)
(e) MW 100M+ (Medisorb 100L available from Medisorb International L.P.)

EXAMPLES

Four biodegradable polymers were melt-spun in combination with various drugs to successfully make compositions useful in the present invention. The polymers used were (1) polyglycolide, a copolymer of L(-) lactide (69.29%) and glycolide (30.05%), (2) p-dioxane, (3) polycaprolactone and (4) polysabacic acid. These polymers were used to encapsulate the drugs vancomycin, gentamicin, tolmentin, diphenhydramine, ibuprofen and insulin, as shown in Table I below.

Each composition was formed by first mixing the drug and a processing aid (medium chain triglyceride supplied by Huls America under the name Miglycol 812) in a mortar and In Example 1, the sample was exposed to 2.7 MRAD/Co 60 for sterilization and then assayed using HPLC for the amount of Vancomycin present. The actual assayed amount (11.26%) substantially matches the theoretical amount (11%) indicating that all of the drug was encapsulated or carried through the melt-spin process with the polymer without apparent degradation.

Figure 1:
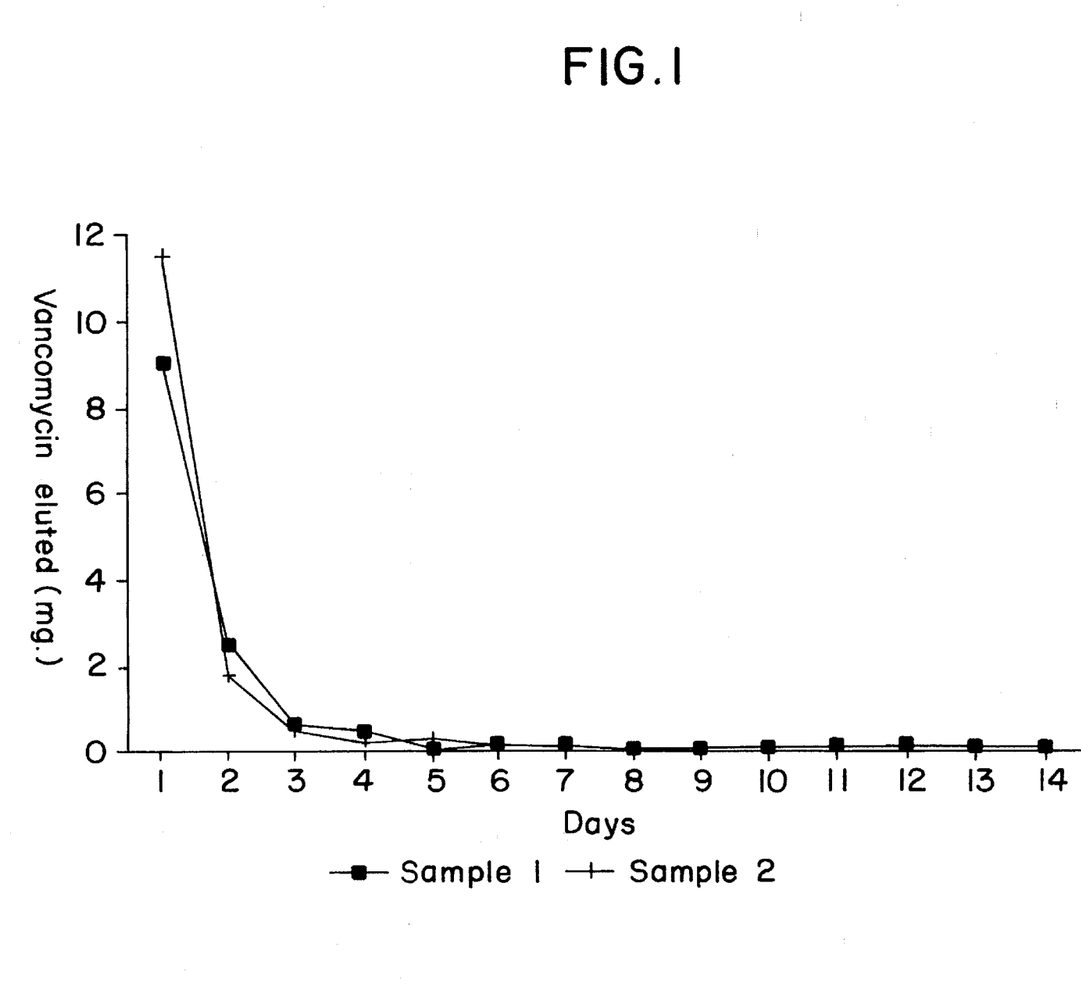
FIG. 1 is a graph showing the amount of vancomycin drug released from the polyglycolide polymer matrix.
Figure 2:
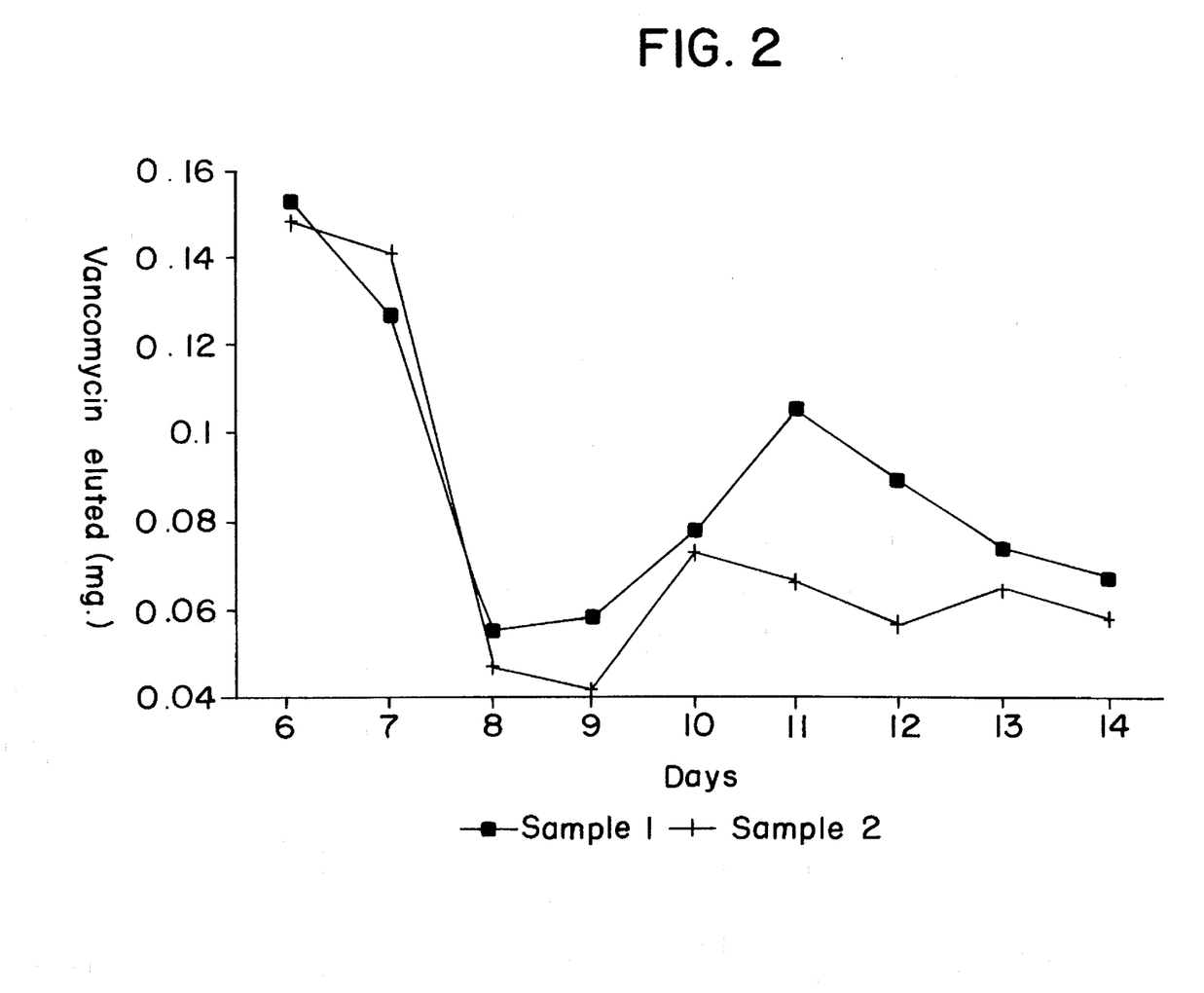
FIG. 2 is an enlargement of a portion of the graph in FIG. 1 to better show the release profile in days 6–14.

The rate of release of Vancomycin from the polymer was then determined through an in vitro extraction study using the following method. The release rates are tabulated in Table II and graphically represented in FIGS. 1 and 2.

A sample of the vancomycin melt-spun polymer product (0.5 g) is placed in the flow unit between filter disks (0.22 um Millipore GV) and maintained at 25° C. Krebs-Ringer buffer (pH 7.4, Sigma Chemical) was pumped from a refrigerated reservoir (5° C.). The solution was warmed at 25° C. before flowing through a filter unit (Millipore Swinnex-47) at a flow rate of 2 ml/h. An initial sample (60 mL) was taken at an accelerated flow rate (30 mL/min.). Fractions were collected (ISCO-Foxy 200) every 24 h and frozen. After 7 days, the fractions are analyzed for vancomycin content. The experiment was continued for an additional 7 days and the remaining polymer was removed from the filter unit, rinsed, dried weighed and the vancomycin content calculated. The results are tabulated below and graphically illustrated in FIGS. 1 and 2.

TABLE II

| VANCOMYCIN ELUTED (mg) | | |
| --- | --- | --- |
| Elapsed Time (Days) | Sample #1 | Sample #2 |
| 0[1] | 1.50 | 4.66 |
| 1 | 7.56 | 6.85 |
| 2 | 2.49 | 1.82 |
| 3 | 0.65 | 0.44 |
| 4 | 0.49 | 0.21 |
| 5 | 0.08 | 0.30 |
| 6 | 0.15 | 0.15 |
| 7 | 0.13 | 0.14 |
| 8 | 0.06 | 0.05 |
| 9 | 0.06 | 0.04 |
| 10 | 0.08 | 0.07 |
| 11 | 0.11 | 0.07 |
| 12 | 0.09 | 0.06 |
| 13 | 0.07 | 0.07 |
| 14 | 0.07 | 0.06 |
| Eluted Vancomycin: | 13.57 mg | 14.99 mg |
| Remaining:[2] | 4.08 mg | 4.08 mg |
| Total: | 17.65 mg | 19.07 mg |
| Initial Sample wt: | 200.26 mg | 200.27 mg |

[1]From initial 60 mL flush.
[2]Vancomycin which remained in the dried polymer at the end of two weeks.

HPLC analysis of fractions was performed using a Beckman System Gold system (Model 126 Pump and Model 166 UV Detector). The column used was a Phenomenex Ultracarb 5u C8 column. The mobil phase composition was comprised of water (81%), acetonitrile (9%) and 0.2M ammonium acetate (10%). UV detection ($\lambda$=214 nm) was employed. The flow rate was 0.8 ml/min. Standard solutions were prepared daily (10, 20 and 30 ug/ml) each time HPLC analysis was performed. All HPLC injections were done in duplicate.

The results demonstrate that a higher concentration of vancomycin was eluted in the first few days of the experiment. The release rate appeared to taper off after 3–4 days. After two days, the amount of vancomycin released per day drops. After six days, vancomycin release begins to level out between 60 and 100 ug. The vancomycin polymer was originally 13.5% vancomycin by weight. After two weeks, the polymer samples were assayed for vancomycin content. Both samples were found to contain 4.08 mg vancomycin which represents 15.1% of the total vancomycin present. 65% of Sample 1 was accounted for while 70% of Sample 2 was recovered. This loss of approximately 30% of the total vancomycin is believed to be due to degradation of the vancomycin over time, when exposed to 5° C. in the fraction collector.

In Examples 2–8, 10, 14 and 15 the melt-spun controlled release product demonstrated successful combination of active (drug) and biodegradable product. In Example 9, the melt-spun product was assayed for gentamicin and it was determined that 89.9% of the theoretical content was present.

Example 11 indicates that the polymer can be melt-spun without the addition of an active and without a Kapton liner.

Example 12 and 13, the presence of insulin in the melt-spun product was confirmed by radioimmunoassay (RIA).

Thus, while there have been disclosed what are presently believed to be the preferred embodiments of the present invention, other and further manifestations of the invention will become apparent to those skilled in the art. It is intended to claim all such changes and modifications which come within the true scope and spirit of the present invention.

What is claimed is:

1. A biodegradable controlled release composition comprising a non-saccharide biodegradable polymer united with a bio-effecting agent formed by flash-flow melt-spin processing said polymer and said bio-effecting agent.

2. The composition of claim 1, wherein the polymer is selected from the group consisting of: poly(glycolic acid), poly(lactic acid), polydioxanes, polyoxalates, poly($\alpha$-esters), polycarbonates, polyanhydrides, polyacetals, polycaprolactones, poly(orthoesters), polyamino acids, polyurethanes, polyiminocarbonates, polyamides, poly(alkyl cyanoacrylates), sebacic acid, polyethylene glycol, polyphosphazene, bis(p-carboxyphenoxy)propane, bis(p-carboxyphenoxy)methane copolymers thereof and mixtures thereof.

3. The composition of claim 2, wherein the bio-effecting agent is useful in the prophylactic or therapeutic treatment of an animal.

4. The composition of claim 3, wherein the bio-effecting agent is selected from the group consisting of angiotensin converting enzyme inhibitors, anti-asthmatics, anti-cholesterolemics, anti-convulsants, anti-depressants, anti-diarrhea preparations, anti-infectives, anti-inflammatory agents, antinauseants, anti-stroke agents, anti-tumor drugs, anti-tussives, anti-uricemic drugs, amino-acid preparations, antiemetics, antiobesity drugs, antiparasitics, antipyretics, appetite stimulants, cerebral dilators, chelating agents, cholecystokinin antagonists, cognition activators, deodorants, dermatological agents, diabetes agents, diuretics, erythropoietic drugs, fertility agents, synthetic hormones, laxatives, mineral supplements, neuroleptics, neuromuscular agents, peripheral vaso-dilators, prostaglandins, vaginal preparations, vaso-constrictors and vertigo agents.

5. The composition of claim 4, wherein the bio-effecting agent is selected from the group consisting of acetaminophen, acetic acid, acetylsalicylic acid, buffered acetylsalicylic acid, albuterol, albuterol sulfate, ethanol isopropanol, allantoin, aloe, aluminum acetate, aluminum carbonate, aluminum chlorohydrate, aluminum hydroxide, alprozolam, amino acids, aminobenzoic acid, amoxicillin, ampicillin, amsacrine, amsalog, anethole, aspartame, atenolol, bacitracin, balsam peru, beclomethasone dipropionate, benzocaine, benzoic acid, benzophenones, benzoyl peroxide, biotin, bisacodyl, bornyl acetate, bromopheniramine maleate, buspirone, caffeine, calamine, calcium, calcium carbonate, calcium casinate, calcium hydroxide, camphor, captopril, cascara sagrada, castor oil, cefaclor, cefadroxil, cephalexin, cetylalcohol, cetylpyridinium chloride, chelated minerals, chloramphenicol, chlorcyclizine hydrochloride, chlorhexidine gluconate, chloroxylenol, chloropentostatin, chlorpheniramine maleate, cholestyramine resin, choline bitartrate, cimetidine hydrochloride, cinnamedrine hydrochloride, citalopram, citric acid, cocoa butter, cod liver oil, codeine and codeine phosphate, clonidine, clonidine hydrochloride, clorfibrate, ciprofloxacin HCl, cyanocobalamin, cyclizine hydrochloride, danthron, dexbrompheniranime maleate, dextromethorphan hydrobromide, diazapam, dibucaine, diclofenac sodium, digoxin, diltiazem, dimethicone, dioxybenzone, diphenhydramine citrate, diphenhydramine hydrochloride, docusate calicum, docusate potassium, docusate sodium, doxycycline hyclate, doxylamine succinate, efaroxan, enalapril, enoxacin, erythromycin, estropipate, ethinyl estradiol, ephedrine, epinephrine bitartrate, erythropoietin, eucalyptol, ferrous fumarate, ferrous gluconate, ferrous sulfate, folic acid, fosphenytoin, fluoxetine HCl, furosemide, gabapentan, gentamicin, gemfibrozil, glipizide, glycerin, glyceryl stearate, griseofulvin, guaifenesin, hexylresorcinol, hydrochlorothiaxide, hydrocodone bitartrate, hydrocortisone, hydrocortisone acetate, 8-hydroxyquinoline sulfate, ibuprofen, indomethacin, inositol, insulin, iodine, ipecac, iron, isoxicam, ketamine, koalin, lactic acid, lanolin, lecithin, lidocaine, lidocaine hydrochloride, lifinopril, liotrix, lovastatin, magnesium carbonate, magnesium hydroxide, magnesium salicylate, magnesium trisilocate, mefenamic acid, meclofenanic acid, meclofenamate sodium, medroxyprogesterone acetate, methenamine mandelate, menthol, meperidine hydrochloride, metaproterenol sulfate, methyl nicotinate, methyl salicylate, methylcellulose, methsuximide, metromidazole, metromidazole hydrochloride, metoprolol tartrate, miconazole nitrate, mineral oil, minoxidil, morphine, naproxen, naproxen sodium, nifedipine, neomycin sulfate, niacin, niacinamide, nicotine, nicotinamide, nitroglycerin, nonoxynol-9, norethindone, norethindone acetate, nystatin, octoxynol, octyl dimethyl PABA, octyl methoxycinnamate, omega-3 polyunsaturated fatty acids, omeprazole, oxolinic acid, oxybenzone, oxtriphylline, para-aminobenzoic acid (PABA), padimate O, paramethadione, pentastatin, peppermint oil, pentaerythriol tetranitrate, pentobarbital sodium, pheniramine maleate, phenobarbital, phenol, phenolphthalein, phenylephrine hydrochloride, phenylpropanolamine, phenylpropanolamine hydrochloride, phenytoin, phenelzine sulfate, pirmenol, piroxicam, polymycin B sulfate, potassium chloride, potassium nitrate, prazepam, procainamide hydrochloride, procaterol, propoxyphene, propoxyphene HCl, propoxyphene napsylate, pramiracetin, pramoxine, pramoxine hydrochloride, propronolol HCl, pseudoephedrine hydrochloride, pseudoephedrine sulfate, pyridoxine, quinapril, quinidine gluconate, quinestrol, ralitoline, ranitadine, resorcinol, riboflavin, salicylic acid, sesame oil, shark liver oil, simethicone, sodium bicarbonate, sodium citrate, sodium fluoride, sodium monofluorophosphate, sulfanethoxazole, sulfur, tacrine, tacrine HCl, theophylline, terfenidine, thioperidone, trimetrexate, triazolam, timolol maleate, tretinoin, tetracycline hydrochloride, tolmetin, tolnaftate, triclosan, triprolidine hydrochloride, undecylenic acid, vancomycin, verapamil HCl, vidaribine phosphate, vitamin A, vitamin B, vitamin C, vitamin D, vitamin E, vitamin K, witch hazel, xylometazoline hydrochloride, zinc, zinc sulfate, and zinc undecylenate.

6. The composition of claim 3 wherein the bioeffecting agent is selected from the group consisting of ache drugs, alkaloids, anti-spasmodics, anticoagulants, contraceptives and hyperglycemic agents.

7. The composition of claim 3 in an oral dosage form.

8. The composition of claim 3 in an implantable dosage form.

9. The composition of claim 3 in a wound treatment dosage form.

10. A controlled release flash-flow melt-spun composition comprising:
   (a) a non-saccharide biodegradable polymer for physically protecting an active agent past the stomach and releasing the active agent in the small intestine; and
   (b) a bio-effecting agent united with said polymer.

11. The composition of claim 10, wherein the polymer is selected from the group consisting of: poly(glycolic acid), poly(lactic acid), polydioxanes, polyoxalates, poly(α-esters), polycarbonates, polyanhydrides, polyacetals, polycaprolactones, poly(orthoesters), polyamino acids, polyurethanes, polyiminocarbonates, polyamide, poly(alkyl cyanoacrylates), sebacic acid, polyethylene glycol, polyphosphazene, bis(p-carboxyphenoxy)propane, bis(p-carboxyphenoxy)methane, copolymers thereof and mixtures thereof.

12. The composition of claim 10, wherein the bio-effecting agent is selected from the group consisting of peptides, antibiotics and mixtures thereof.

13. The composition of claim 12, wherein the bio-effecting agent is insulin.

14. A controlled release flash flow melt-spun composition for treatment of ruminants comprising: a) a non-saccharide biodegradable polymer which is protective of an active in the environment of the rumen at pH of about 5 or more but which releases the active in environment of the abomasum at pH of about 3.5 or less; and b) a bio-effecting active united with said polymer.

15. The composition of claim 14, wherein the active is a therapeutic, prophylactic or nutritive agent.

16. The composition of claim 14, wherein the active is selected from the group consisting of antibiotics, amino-acids, hormones and mixtures thereof.

17. A method of treating an animal comprising administering to said animal a flash flow melt-spun controlled release composition comprising a non-saccharide biodegradable polymer and a bio-effecting therapeutic or prophylactic active.

18. The method of claim 17, wherein the polymer is selected from the group consisting of: poly(glycolic acid), poly(lactic acid), polydioxanes, polyoxalates, poly(α-esters), polycarbonates, polyanhydrides, polyacetals, polycaprolactones, poly(orthoesters), polyamino acids, polyurethanes, polyiminocarbonates, polyamides, poly(alkyl cyanoscrylates), sebacic acid, polyethylene glycol, polyphosphazene, bis(p-carboxyphenoxy)propane, bis(p-carboxyphenoxy)methane copolymers thereof and mixtures thereof.

19. The composition of claim 17, wherein the bio-effecting agent is selected from the group consisting of acetaminophen, acetic acid, acetylsalicylic acid and its buffered form, albuterol, and albuterol sulfate, ethanol isopropanol, allantoin, aloe, aluminum acetate, aluminum carbonate, chlorohydrate, hydroxide, alprozolam, amino acids, aminobenzoic acid, amoxicillin, ampicillin, amsacrine, amsalog, anethole, aspartame, atenolol, bacitracin, balsam peru, beclomethasone dipropionate, benzocaine, benzoic acid, benzophenones, benzoyl peroxide, biotin, bisacodyl, bornyl acetate, bromopheniramine maleate, buspirone, caffeine, calamine, calcium, calcium carbonate, calcium casinate, calcium hydroxide, camphor, captopril, cascara sagrada, castor oil, cefaclor, cefadroxil, cephalexin, cetylalcohol, cetylpyridinium chloride, chelated minerals, chloramphenicol, chlorcyclizine hydrochloride, chlorhexidine gluconate, chloroxylenol, chloropentostatin, chlorpheniramine maleate, cholestyramine resin, choline bitartrate, cimetidine hydrochloride, cinnamedrine hydrochloride, citalopram, citric acid, cocoa butter, cod liver oil, codeine and codeine phosphate, clonidine, clonidine hydrochloride, clorfibrate, ciprofloxacin HCl, cyanocobalamin, cyclizine hydrochloride, danthron, dexbrompheniranime maleate, dextromethorphan hydrobromide, diazapam, dibucaine, diclofenac sodium, digoxin, diltiazem, dimethicone, dioxybenzone, diphenhydramine citrate, diphenhydramine hydrochloride, docusate calicum, docusate potassium, docusate sodium, doxycycline hyclate, doxylamine succinate, efaroxan, enalapril, enoxacin, erythromycin, estropipate, ethinyl estradiol, ephedrine, epinephrine bitartrate, erythropoietin, eucalyptol, ferrous fumarate, ferrous gluconate, ferrous sulfate, folic acid, fosphenytoin, fluoxetine HCl, furosemide, gabapentan, gentamicin, gemfibrozil, glipizide, glycerin, glyceryl stearate, griseofulvin, guaifenesin, hexylresorcinol, hydrochlorothiaxide, hydrocodone bitartrate, hydrocortisone, hydrocortisone acetate, 8-hydroxyquinoline sulfate, ibuprofen, indomethacin, inositol, insulin, iodine, ipecac, iron, isoxicam, ketamine, koalin, lactic acid, lanolin, lecithin, lidocaine, lidocaine hydrochloride, lifinopril, liotrix, lovastatin, magnesium carbonate, magnesium hydroxide, salicylate, magnesium trisilocate, mefenamic acid, meclofenanic acid, meclofenamate sodium, medroxyprogesterone acetate, methenamine mandelate, menthol, meperidine hydrochloride, metaproterenol sulfate, methyl nicotinate, methyl salicylate, methylcellulose, methsuximide, metromidazole, metromidazole hydrochloride, metoprolol tartrate, miconazole nitrate, mineral oil, minoxidil, morphine, naproxen, naproxen sodium, nifedipine, neomycin sulfate, niacin, niacinamide, nicotine, nicotinamide, nitroglycerin, nonoxynol-9, norethindone, norethindone acetate, nystatin, octoxynol, octyl dimethyl PABA, octyl methoxycinnamate, omega-3 polyunsaturated fatty acids, omeprazole, oxolinic acid, oxybenzone, oxtriphylline, para-aminobenzoic acid (PABA), padimate O, paramethadione, pentastatin, peppermint oil, pentaerythriol tetranitrate, pentobarbital sodium, pheniramine maleate, phenobarbital, phenol, phenolphthalein, phenylephrine hydrochloride, phenylpropanolamine, phenylpropanolamine hydrochloride, phenytoin, phenelzine sulfate, pirmenol, piroxicam, polymycin B sulfate, potassium chloride, potassium nitrate, prazepam, procainamide hydrochloride, procaterol, propoxyphene, propoxyphene HCl, propoxyphene napsylate, pramiracetin, pramoxine, pramoxine hydrochloride, propronolol HCl, pseudoephedrine hydrochloride, pseudoephedrine sulfate, pyridoxine, quinapril, quinidine gluconate, quinestrol, ralitoline, ranitadine, resorcinol, riboflavin, salicylic acid, sesame oil, shark liver oil, simethicone, sodium bicarbonate, sodium citrate, sodium fluoride, sodium monofluorophosphate, sulfanethoxazole, sulfur, tacrine, tacrine HCl, theophylline, terfenidine, thioperidone, trimetrexate, triazolam, timolol maleate, tretinoin, tetracycline hydrochloride, tolmetin, tolnaftate, triclosan, triprolidine hydrochloride, undecylenic acid, vancomycin, verapamil HCl, vidaribine phosphate, vitamin A, vitamin B, vitamin C, vitamin D, vitamin E, vitamin K, witch hazel, xylometazoline hydrochloride, zinc, zinc sulfate, and zinc undecylenate.

20. The method of claim 17, wherein the polymer is erodible in the presence of animal body fluids.

21. A flash-flow melt-spun drug delivery system capable of controllably releasing a pharmaceutically active agent in an animal comprising a non-saccharide biodegradable polymer and a pharmaceutically active agent wherein the polymer is in predominantly amorphous form and is united with said active agent.

22. A method of preparing a controlled release pharmaceutical composition comprising subjecting a mixture of a biodegradable non-saccharide polymer and a pharmaceutically active agent to flash-flow melt-spinning to unite said polymer and active under conditions which produce a solid capable of releasing said active in an animal.

23. A device for promoting the growth of living tissue comprising a biocompatable or implantable support structure impregnated or coated with a biodegradable controlled release flash-flow melt-spun composition comprising a non-saccharide biodegradable polymer united with a growth regulator.

24. The device of claim 23, wherein the growth regulator is selected from the group consisting of human growth hormone, bovine growth hormone and porcine growth hormone.

25. A method of making a device for promoting the growth of living tissue comprising (i) flash-flow melt-spinning a composition comprising a non-saccharide biodegradable polymer and a growth regulator and (ii) collecting said composition on a support structure.

26. The composition of claim 3, wherein the bio-effecting agent is selected from the group consisting of anti-histamines, anti-manics, anti-viral agents, anesthetics, antacids, anti-arthritics, anti-biotics, anti-psychotics, anti-spasmodics, anxiolytic agents, appetite suppressants, cardiovascular agents, cough suppressants, emollients, gastro-intestinal agents, growth regulators, hypoglycemic agents, respiratory stimulants, and vitamins.

27. The method of claim 17, wherein the bioeffecting agent is selected from the group consisting of anti-histamines, anti-manics, anti-viral agents, anesthetics, antacids, anti-arthritics, anti-biotics, anti-psychotics, anti-spasmodics, anxiolytic agents, appetite suppressants, cardiovascular agents, cough suppressants, emollients, gastro-intestinal agents, growth regulators, hypoglycemic agents, respiratory stimulants, and vitamins.

28. A sustained release solid composition formed by flash-flow melt-spin processing a solid non-saccharide biodegradable polymer and a solid bio-effecting agent.

* * * * *